United States Patent [19]

Frank

[11] Patent Number: 5,095,152
[45] Date of Patent: Mar. 10, 1992

[54] NOVEL HEPTAMETHYL INDANE COMPOUND

[75] Inventor: Walter C. Frank, Holland, Pa.

[73] Assignee: Union Camp Corporation, Wayne, N.J.

[21] Appl. No.: 618,356

[22] Filed: Nov. 21, 1990

[51] Int. Cl.$^5$ .............................................. C07C 47/23
[52] U.S. Cl. ...................................... 568/440; 512/17
[58] Field of Search ................... 568/440, 327; 512/17

[56] References Cited

U.S. PATENT DOCUMENTS

| | | | |
|---|---|---|---|
| 3,278,622 | 10/1966 | Stofberg et al. | 568/440 |
| 3,509,215 | 4/1970 | Wood et al. | 512/17 |
| 4,162,256 | 7/1979 | Sprucker et al. | 568/327 |
| 4,352,748 | 10/1982 | Traas et al. | 568/327 |
| 4,568,782 | 2/1986 | Pognotta et al. | 568/327 |

FOREIGN PATENT DOCUMENTS 50-40701 4/1975 Japan ..................................... 512/17

OTHER PUBLICATIONS

Fehr et al., Helv. Chem. Acta, vol. 72, pp. 1537–1553 (1989).

Primary Examiner—James H. Reamer
Attorney, Agent, or Firm—William K. Wissing

[57] ABSTRACT

The present invention relates to a novel indane compound which is 5-formyl-1,1,2,3,3,4,6-heptamethylindane, a compound of the formula

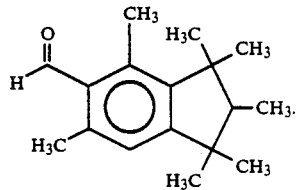

1 Claim, No Drawings

NOVEL HEPTAMETHYL INDANE COMPOUND

BACKGROUND OF THE INVENTION

The present invention relates to a novel acylated heptamethyl indane compound having a fragrant musk-like aroma.

Musk fragrances are in great demand for use in various products such as in perfumes, colognes, cosmetics, soaps and others. However, natural musk, which is obtained from the Asian musk deer, is extremely scarce and is quite expensive. Accordingly, fragrance chemists have spent considerable time searching for synthetic products which duplicate or closely simulate this natural musk scent.

As a result of these research efforts, a number of different synthetic musks have been discovered. Among such synthetic compounds are the acetyl indanes described by U.S. Pat. No. 4,466,908, compounds of the formulas

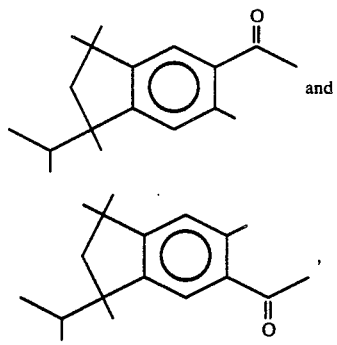

and which may be employed, if desired, in combination with acetyl tetrahydronaphthalenes of the formula

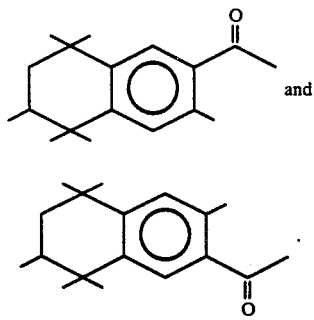

and

Similarly, Fehr et al., *Helvetica Chimica Acta*, Vol. 72, pp. 1537-1553 (1989) discusses such synthetic musks as those of the formula

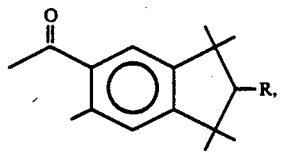

wherein R is either H or $CH_3$.

U.S. Pat. No. 4,352,748 discloses formylated and acetylated indane musks, including those of the formulas

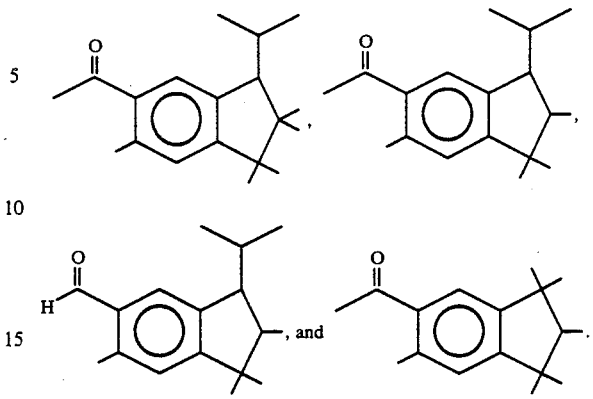

Other acetyl indanes, such as 6-acetyl-1,1,3,3,5-pentamethylindane, 5-acetyl-1,1,2,3,3-pentamethylindane and 6-acetyl-5-ethyl-1,1,2,3,3-pentamethylindane, are disclosed in French Patent No. 1,392,804 (as reported in Chemical Abstracts, Vol. 63, p. 1681d (1965)).

European Patent Publication 0 301 375 A2 describes formylated tetralins, such as 1,1,2,4,4-pentamethyl-6-formyl-1,2,3,4-tetrahydronaphthalene, and their utility as synthetic musks.

New and or better musk aroma compounds are needed. The present invention is directed to this important end.

SUMMARY OF THE INVENTION

The present invention provides a novel indane compound which is 5-formyl-1,1,2,3,3,4,6-heptamethylindane, a compound of the formula

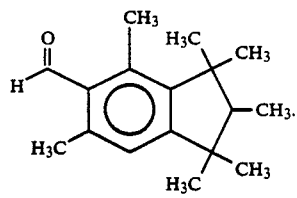

The foregoing compound is an active musk aroma fragrance having utility in the perfumery and/or other industries. The compound of the invention can be used alone or in combination with other compounds or ingredients.

DETAILED DESCRIPTION OF THE INVENTION

The novel heptamethyl indane compound of the invention, 5-formyl-1,1,2,3,3,4,6-heptamethylindane, can be prepared in various fashions.

In the preferable protocol for preparing the unformylated moiety, 1,1,2,3,3,4,6-heptamethylindane, 5-isopropyl-meta-xylene and 2-methyl-2-butene are employed as reactants. Other reactant combinations include 5-isopropenyl-meta-xylene and 2-methyl-2-butene, or alternatively, meta-xylene and 2,4-dichloro-2,3,4-trimethylpentane. The foregoing reactants can be synthesized using conventional organic synthesis procedures. The reactants can then be combined with a Lewis acid, a solvent which can be a halogenated or unhalogenated solvent, and optionally, a phase transfer agent, to form 1,1,2,3,3,4,6-heptamethylindane.

Any of the Lewis acids, that is, any non-protonic compounds capable of accepting an electron pair, are suitable for use in the foregoing process. Exemplary Lewis acids include metal halides such as aluminum halides, including aluminum chloride, aluminum bromide, aluminum iodide, monofluorodichloroaluminum, monobromodichloroaluminum and monoiododichloroaluminum. Alkyl metals and alkyl metal halides suitable for use as Lewis acids in the present process are disclosed, for example, in Kennedy, Joseph P., *Carbocationic Polymerization,* p. 221 (Wiley-Interscience Publishers, 1982), the disclosures of which are incorporated herein by reference. In the subject process, aluminum halides are preferred. Of the aluminum halides, aluminum chloride and aluminum bromide, particularly aluminum chloride ($AlCl_3$), are most preferred.

Halogenated solvents suitable for use in the process are varied, and include halogenated aliphatic, halogenated alicyclic and halogenated aromatic hydrocarbon solvents. Particularly preferred are the halogenated aliphatic hydrocarbons. Suitable halogenated solvents include, for example, 1,2-dichloroethane, 1,1-dichloroethane, trichloromethane, dichloromethane, 1,1,2,2-tetrachloroethylene, 1,2-dichloroethylene, 1,2,3-trichloropropane, 1,1,2-trichloroethane, monochlorobenzene, fluorobenzene, and orthodichlorobenzene. Particularly preferred halogenated solvents include dichloromethane, trichloromethane and 1,2-dichloroethane.

As an alternative to or in combination with halogenated solvents, one may employ unhalogenated solvents. A variety of unhalogenated solvents may be utilized, including, unhalogenated aliphatic, unhalogenated alicyclic and unhalogenated aromatic hydrocarbon solvents. Such unhalogenated solvents are generally preferred over the halogenated solvents for reasons of safety. Particularly preferred are the unhalogenated aliphatic and unhalogenated alicyclic hydrocarbons. Suitable unhalogenated solvents include, for example, the aliphatic hydrocarbon solvents n-hexane, n-heptane and n-octane, the alicyclic hydrocarbon solvent cyclohexane, and aromatic hydrocarbon solvents, such as mesitylene. A particularly preferred unhalogenated solvent is the unhalogenated alicyclic hydrocarbon solvent cyclohexane.

Phase transfer agents suitable for use in the process include onium salts such as ammonium, phosphonium and sulfonium salts. Other phase transfer agents suitable for use in the present process will be readily apparent to those skilled in the art, once having been made aware of the present disclosure.

Examples of ammonium phase transfer agents include quaternary ammonium halides such as methyltrioctylammonium chloride, methyltrinonylammonium chloride, methyltridecylammonium chloride, hexadecyltrihexylammonium bromide, ethyltrioctylammonium bromide, didodecyldimethylammonium chloride, tetraheptylammonium iodide, dioctadecyldimethylammonium chloride, tridecylbenzylammonium chloride, and homologues thereof having chlorine, fluorine, bromine or iodine atoms substituted for the enumerated halide atom.

Exemplary phosphonium phase transfer agents include quaternary phosphonium halides such as tributyldecylphosphonium iodide, triphenyldecylphosphonium iodide, tributylhexadecylphosphonium iodide, and homologues thereof having chlorine, fluorine or bromine atoms substituted for the iodine atom.

Representative sulfonium phase transfer agents include ternary sulfonium halides such as lauryldimethylsulfonium iodide, lauryldiethylsulfonium iodide and tri(n-butyl)sulfonium iodide, and homologues thereof having chlorine, fluorine or bromine atoms substituted for the iodine atom.

These and other suitable phase transfer agents are described, for example, in Napier et al., U.S. Pat. No. 3,992,432 entitled "Phase Transfer Catalysis of Heterogenous Reactions by Quaternary Salts", and in Kondo et al., *Synthesis,* pp. 403–404 (May 1988), the disclosures of which are incorporated herein by reference.

Preferable phase transfer agents are ammonium or sulfonium salts, particularly quaternary ammonium or ternary sulfonium halides. Most preferred are quaternary ammonium halides, particularly methyltrioctylammonium chloride, and a mixture of methyltrioctylammonium chloride and methyltridecylammonium chloride. The latter mixture is marketed under the trademark Adogen-464, by Sherex Co., located in Dublin, Ohio.

In general, the molar proportions of the reagents employed in the process can be varied over a relatively wide range, the particular amount to be employed being well within the ambit of those skilled in the art, once armed with the present disclosures. For best results, however, it is important to maintain a ratio of less than one mole of phase transfer agent per mole of Lewis acid. Preferably, the molar ratio is about 0.8 to 1.0, more preferably about 0.5 to 1.0, phase transfer agent to Lewis acid. It should be noted that some phase transfer agents sold commercially are sold in an impure form. Such impurities usually comprise water or an alcohol species. Water and alcohol, as well as other impurities, will react adversely with the Lewis acid, thereby lowering the amount of Lewis acid available for the process of the present invention. Accordingly, where the phase transfer agent added contains such impurities, the amount of Lewis acid should be increased to account for these impurities. In such a situation, the ratio of transfer agent to Lewis acid might be about 0.3 to 1.0. Such impure agent-containing mixtures are referred to herein as mixtures in an "impure form".

The process can be carried out in any suitable vessel which provides sufficient contacting between the Lewis acid, the phase transfer agent and the reactants. For simplicity, a stirred batch reactor can be employed. Although stirring is recommended to provide efficient contact between reactants, it has been found that in the halogenated solvent, or in the unhalogenated solvent plus phase transfer agent and/or solvent, the Lewis acid is able to solubilize rather quickly, thereby obviating the need for stringent stirring requirements. The reaction vessel used should be resistant to the possible corrosive nature of the Lewis acid. Glass-lined vessels are suitable for this purpose, as well as other vessel materials well-known in the art.

The reagents may be added to the vessel in any order, although generally the solvent, the reactants and any phase transfer agent are added first, followed by Lewis acid addition.

Ideally, the reaction is carried out at temperatures ranging from about $-30°$ C. to about 50° C., preferably temperatures ranging from about $-10°$ C. to about 30° C., and most preferably at temperatures ranging from about 0° C. to about 20° C.

The pressure at which the reaction is carried out is not critical. If the reaction is carried out in a sealed vessel, autogenous pressure is acceptable, although higher or lower pressures, if desired, may be employed. The reaction may also be carried out at atmospheric pressure in an open reaction vessel, in which case, the vessel is preferably equipped with a moisture trap to prevent significant exposure of Lewis acid to moisture. The reaction may take place in an oxygen atmosphere or an inert atmosphere, as in the presence of a gas such as nitrogen, argon and the like, the type of atmosphere also not being critical.

Reaction time is generally rather short and is often dictated by the type of equipment employed. Sufficient time should be provided, however, for thorough contacting of the reactants, the Lewis acid, the solvent, and any phase transfer employed. Generally, the reaction proceeds to equilibrium in about 1 to about 8 hours.

Product can be recovered from the reaction mixture by first quenching the reaction mixture in cold water or on crushed ice, preferably on ice, and then processing the mixture in the usual manner for Friedel-Crafts reactions to extract the 1,1,2,3,3,4,6-heptamethylindane compound. Suitable extraction protocol is described, for example, in George A. Olah, *Friedel-Crafts And Related Reactions*, Vols. 1 and 2 (Interscience Publishers, John Wiley and Sons, 1964). Typically, following quenching and the resultant phase separation, the organic layer is washed an additional time with water to aid in removal of the Lewis acid. One or more additional washings can be carried out with dilute alkali solution to further aid Lewis acid removal.

The 1,1,2,3,3,4,6-heptamethylindane compound thus prepared can then be formylated, that is, converted to 5-formyl-1,1,2,3,3,4,6-heptamethylindane, using conventional formylation technology, producing a compound having a very fine, musk-like fragrance, a characteristic which renders it highly valuable for use in the perfumery industry.

Specifically, to produce the 5-formyl-1,1,2,3,3,4,6-heptamethylindane compound of the invention, the 1,1,2,3,3,4,6-heptamethylindane compound can be reacted with $\alpha,\alpha$-dichloromethyl methyl ether, in an organic solvent, preferably a halogenated organic solvent such as, for example, anhydrous methylene chloride. Other suitable halogenated solvents are as discussed above in connection with the preparation of the 1,1,2,3,3,4,6-heptamethylindane compound. Such formylation methods are well known in the art and are described, for example, in *Organic Synthesis, Collective Vol. 5*, pp. 49–50 (John Wiley & Sons, 1973), the disclosures of which are incorporated herein by reference, in their entirety.

The 5-formyl-1,1,2,3,3,4,6-heptamethylindane compound of the invention has high utility in the fragrance industry. This compound can be used alone or in combination with one or more ingredients to provide a sweet, musky fragrance.

For example, the 5-formyl-1,1,2,3,3,4,6-heptamethylindane compound of the invention may be used as olfactory components in anionic, cationic, nonionic and zwitterionic detergents, soaps, fabric softener compositions, fabric softener articles for use in clothes dryers, space odorants and deodorants, perfumes, colognes, toilet water, bath preparations, deodorants, cosmetics, hand lotions, sunscreens, powders, as well as in other ways. The amount of the heptamethyl indane to be used in augmenting or enhancing the aroma of an article or composition will vary depending upon the particular use intended, as will be readily apparent to those skilled in the art. Generally, however, the indane is employed in an amount of about 0.05 percent by weight of the perfumed article up to about 30 percent by weight of the perfumed article. In addition, the perfumed composition or fragrance composition of the invention can contain a vehicle or carrier. Such vehicles or carriers include liquids such as a non-toxic alcohol, a non-toxic glycol, or the like. An example of a non-toxic alcohol is ethyl alcohol. An example of a non-toxic glycol is 1,2-propylene glycol. Alternatively, the vehicle or carrier can be an absorbent solid such as a gum, e.g., gum arabic, xantham gum or guar gum, or components for encapsulating a composition such as gelatin, by means of coacervation or such as a urea formaldehyde polymer whereby a polymeric shell is formed around a liquid perfume oil center. The amount of the vehicle or carrier will vary depending upon the particular use intended, as will be readily apparent to those skilled in the art. However, the vehicle or carrier can generally be employed in an amount of about 5 percent by weight up to about 95 percent by weight of the preferred composition.

The present invention is further described in the following Examples. These Examples are not to be construed as limiting the scope of the appended claims.

In each Example, results were analyzed on both polar and non-polar gas chromatography columns. All gas chromatography analyses were carried on capillary columns using a weight percent internal standard method of analysis. Structural identifications were assigned based on GCMS fragmentation patterns compared to standards.

Example 1 describes the preparation of 1,1,2,3,3,4,6-heptamethylindane. Example 2 discusses the synthesis of 5-formyl-1,1,2,3,3,4,6-heptamethylindane from the 1,1,2,3,3,4,6-heptamethylindane of Example 1.

EXAMPLES

Example 1

A 100 ml four-necked round bottom flask equipped with an $N_2$ line, condenser, thermocouple-temperature controller, and addition funnel was charged with $CH_2Cl_2$ (9.79 g), and cooled to 15° C. with a dry ice/isopropanol bath. To the flask was then added, with stirring, anhydrous $AlCl_3$ (0.874 g). While maintaining a temperature of 15° C., a homogeneous mixture of 5-isopropyl-meta-xylene (21.7 g, 0.1466 moles) and 2-methyl-2-butene (20.53 g, 0.2932 moles) was added to the flask over a period of about 30 minutes. The reaction was then allowed to proceed for about 2 additional hours at the same temperature. The flask contents were continuously stirred throughout the reaction.

The reaction was then quenched with cold deionized water (10 ml), and the resultant product further treated with 10% aqueous $NaHCO_3$ and extracted with $CH_2Cl_2$. After drying with anhydrous $Na_2SO_4$, the organic solution was rotoevaporated to give about 30 g of crude product containing about 50 weight percent of 1,1,2,3,3,4,6-heptamethylindane.

Example 2

To a 1 l three-necked flask equipped with a reflux condenser, a stirrer, and a dropping funnel, was charged 21.6 g of the crude product containing about 50 weight percent 1,1,2,3,3,4,6-heptamethylindane from Example 1, and 115 ml anhydrous $CH_2Cl_2$. The solution was then cooled in an ice bath, and 31.61 g (18.3 ml, 0.166 moles)

TiCl₄ was added over a period of about 3 minutes. While the solution is stirred and cooled, 9.53 g (7.5 ml, 0.083 moles) α,α-dichloromethyl methyl ether was added dropwise over a 10 minute period, while maintaining a temperature of about 0° to about 5° C. After the addition is complete, the mixture is stirred for about 20 minutes in an ice bath, for about 30 minutes without cooling, and finally for about 15 minutes at 35° C.

The reaction mixture was then poured into a separatory funnel containing about 0.2 kg of crushed ice and shaken thoroughly. The organic layer is separated, and the aqueous solution is extracted with two 50 ml portions of methylene chloride. The combined organic solution is washed three times with 50 ml portions of water. A crystal of hydroquinone is added to the methylene chloride solution which is then dried over anhydrous sodium sulfate. After evaporation of the solvent, the residue is distilled to give 21.82 g of crude product containing 53.5% of 5-formyl-1,1,2,3,3,4,6-heptamethylindane.

Various modifications of the invention, in addition to those shown and described herein, will be apparent to those skilled in the art from the foregoing description. Such modifications are also intended to fall within the scope of the appended claims.

What is claimed is:

1. A compound of the formula:

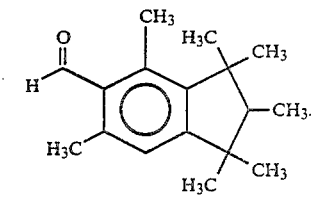

* * * * *